United States Patent
Berry (10) Patent No.: US 6,723,126 B1
(45) Date of Patent: Apr. 20, 2004

(54) LATERALLY EXPANDABLE CAGE

(75) Inventor: Bret Berry, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/285,723

(22) Filed: Nov. 1, 2002

(51) Int. Cl.$^7$ ................ A61F 2/44; A61F 2/46
(52) U.S. Cl. ................ 623/17.11; 623/23.47; 606/61; 606/99
(58) Field of Search .......... 623/17.11, 17.15, 623/17.16, 23.47, 23.5, 23.53; 606/61, 99

(56) References Cited

U.S. PATENT DOCUMENTS

| | | | |
|---|---|---|---|
| 4,349,921 A | * 9/1982 | Kuntz | 623/17.16 |
| 4,401,112 A | 8/1983 | Rezaian | 128/92 |
| 4,553,273 A | 11/1985 | Wu | 623/18 |
| 4,863,476 A | 9/1989 | Shepperd | 623/17 |
| 5,336,223 A | 8/1994 | Rogers | 606/61 |
| 5,397,364 A | 3/1995 | Kozak et al. | 623/17 |
| 5,554,191 A | 9/1996 | Lahille et al. | 623/17 |
| 5,653,763 A | 8/1997 | Errico et al. | 623/17 |
| 5,693,100 A | 12/1997 | Pisharodi | 623/17 |
| 6,008,431 A | * 12/1999 | Caldarise et al. | 623/16 |
| 6,039,761 A | 3/2000 | Li et al. | 623/17 |
| 6,080,193 A | 6/2000 | Hochshuler et al. | 623/17 |
| 6,110,210 A | 8/2000 | Norton et al. | 623/17.16 |
| 6,176,882 B1 | * 1/2001 | Biedermann et al. | 623/17.15 |
| 6,190,414 B1 | * 2/2001 | Young et al. | 623/17.15 |
| 6,193,757 B1 | 2/2001 | Foley et al. | 623/17.16 |
| 6,206,923 B1 | 3/2001 | Boyd et al. | 623/17.11 |
| 6,419,705 B1 | * 7/2002 | Erickson | 623/17.16 |
| 6,451,057 B1 | * 9/2002 | Chen et al. | 623/17.15 |
| 6,468,311 B2 | * 10/2002 | Boyd et al. | 623/17.16 |
| 6,478,823 B1 | * 11/2002 | Michelson | 623/17.16 |
| 2001/0020186 A1 | * 9/2001 | Boyce et al. | 623/17.16 |
| 2002/0040243 A1 | 4/2002 | Attali et al. | 623/17.16 |

FOREIGN PATENT DOCUMENTS

WO    WO 97/00054    1/1997    ............ A61F/2/44

* cited by examiner

Primary Examiner—Eduardo C. Robert
Assistant Examiner—David Comstock
(74) Attorney, Agent, or Firm—Woodard, Emhardt, Moriarty, McNett & Henry LLP (57) ABSTRACT

A laterally expandable spinal implant includes a central body and two wings that are adapted to be received within an inner chamber formed within the central body. The wings have guide rails that fit into grooves defined in the central body. To ensure that the implant is properly secured, each guide rail has an outer end with a cutting surface that cuts into vertebral end plates when the wings are extended. The two wings are connected together through a central turnbuckle shaft that has geared teeth and threading on both ends that engage threaded cavities in the wings. Through the gear teeth, the turnbuckle shaft is able to be rotated so as to laterally extend the wings from the central member. A locking mechanism locks the turnbuckle shaft to prevent the wings from retracting.

38 Claims, 7 Drawing Sheets

LATERALLY EXPANDABLE CAGE

BACKGROUND

The present invention generally concerns spinal implants, and more specifically, but not exclusively, concerns a laterally expandable vertebral implant.

A major cause of persistent, often disabling, back pain can arise by disruption of the disc annulus, chronic inflammation of the disc, or relative instability of vertebral bodies surrounding a given disc, such as might occur due to a degenerative disease. In the more severe cases, some form of mechanical limitation to the movement of the vertebrae on either side of the subject disc is necessary. In such cases, the disc tissue is irreparably damaged, thereby necessitating removal of the entire disc. However, when the disc nucleus is removed without subsequent stabilization the same disabling back pain often reoccurs due to persistent inflammation and/or instability.

Various approaches have been developed to stabilize the adjacent vertebral bodies following excision of this material. In one approach, two adjacent vertebrae are fused together through a fusion device that is implanted between the vertebrae. Many of these existing implant designs have drawbacks that lower the spinal fusion rates. Among these design drawbacks, one such flaw is that the implants subside into the vertebral end plates, thereby reducing the spacing between the vertebral bodies. With prior fusion devices, and even some prosthetic devices, a large portion of the load is placed against the weakest part of the vertebral body, which can lead to cavitation of the device into the surrounding vertebral endplates with subsequent collapse of the inner discal space and even damage of the vertebrae itself. Another frequent cause for subsistence is created by having a small area of contact between the implant and the endplates. As one should appreciate, the less surface area of contact between the implant and the end plates, the greater the risk of subsistence.

Another flaw of many implants is the lack of stability created after implantation. Stability is crucial to the success of a fusion. The implant must be securely fixated to the vertebral bodies in order to ensure that no movement occurs between the two. If movement does occur between the vertebral bodies and the implant, the bone may not properly fuse, thereby creating stability problems. Moreover, some designs limit the amount of graft material, which may be able to be used with the implant. The larger area of graft material that is able to contact the endplates, the better chances of a good, solid bone growth between the two vertebrae.

Some designs have created implants in which the majority of the implant is positioned over the harder cortical bone of the apophyseal ring of the vertebrae in order to reduce the chances of subsistence. However, with these designs, the implant is made from multiple separate components that are individually assembled together within the disc space. Each component is implanted separately and then attached to one another within the disc space. As should be appreciated, assembling such an implant in the disc space can be rather difficult. Such implants also tend to lack a stiff central body, which is essential to the stability of the implant as well as entire fusion construct. Moreover, such implants have no mechanism to fix the implant to the vertebral body. Typically, one has to use bone screws to secure the implant to the vertebral bodies, which makes the implantation process more complicated and difficult. In addition, such implants generally have a single lateral width, and therefore, it is generally very difficult, if not impossible, to adjust for differently sized vertebrae. Another flaw is that these designs typically do not provide a mechanism for ensuring that the spacers are properly positioned. Since the lateral spacers of these types of implants are independently assembled within the disc space, the lateral members can be positioned at unequal positions along the apophyseal ring, thereby increasing the risk that the implant will subside into the vertebral end plates.

SUMMARY

In one aspect, a spinal implant includes a cage defining an interior cavity and an expansion mechanism received in the cavity of the cage. A pair of wings are operatively coupled to the expansion mechanism, and the wings each have opposing vertebrae engaging surfaces that are configured to engage opposing vertebrae. The expansion mechanism is operable to laterally move the wings between the vertebrae from a compact configuration in which at least a majority of the wings are received in the cavity of the cage to an expanded configuration in which the wings extend from the cage with the vertebrae engaging surfaces on each of the wings engaging the vertebrae.

Another aspect concerns a fusion device for implanting between opposing vertebrae that define a disc space. The device includes a central member and at least one pair of lateral members slidably coupled to the central member. The device further includes means for extending the lateral members from the central member into the disc space between the vertebrae with each of the lateral members engaging both of the vertebrae.

In a further aspect, an apparatus includes a spinal implant. The spinal implant includes a central member defining an interior cavity and a pair of openings defined on opposite sides of the central member that open into the interior cavity. A pair of wings are slidably received in the openings in the central member. A shaft is coupled to the wings, and the shaft has at least one threaded portion threadedly engaging at least one of the wings.

DETAILED DESCRIPTION

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates. Some embodiments of the invention are shown in great detail, although it will be apparent to those skilled in the relevant art that some of the features may not be shown for the sake of clarity.

Figure 1:
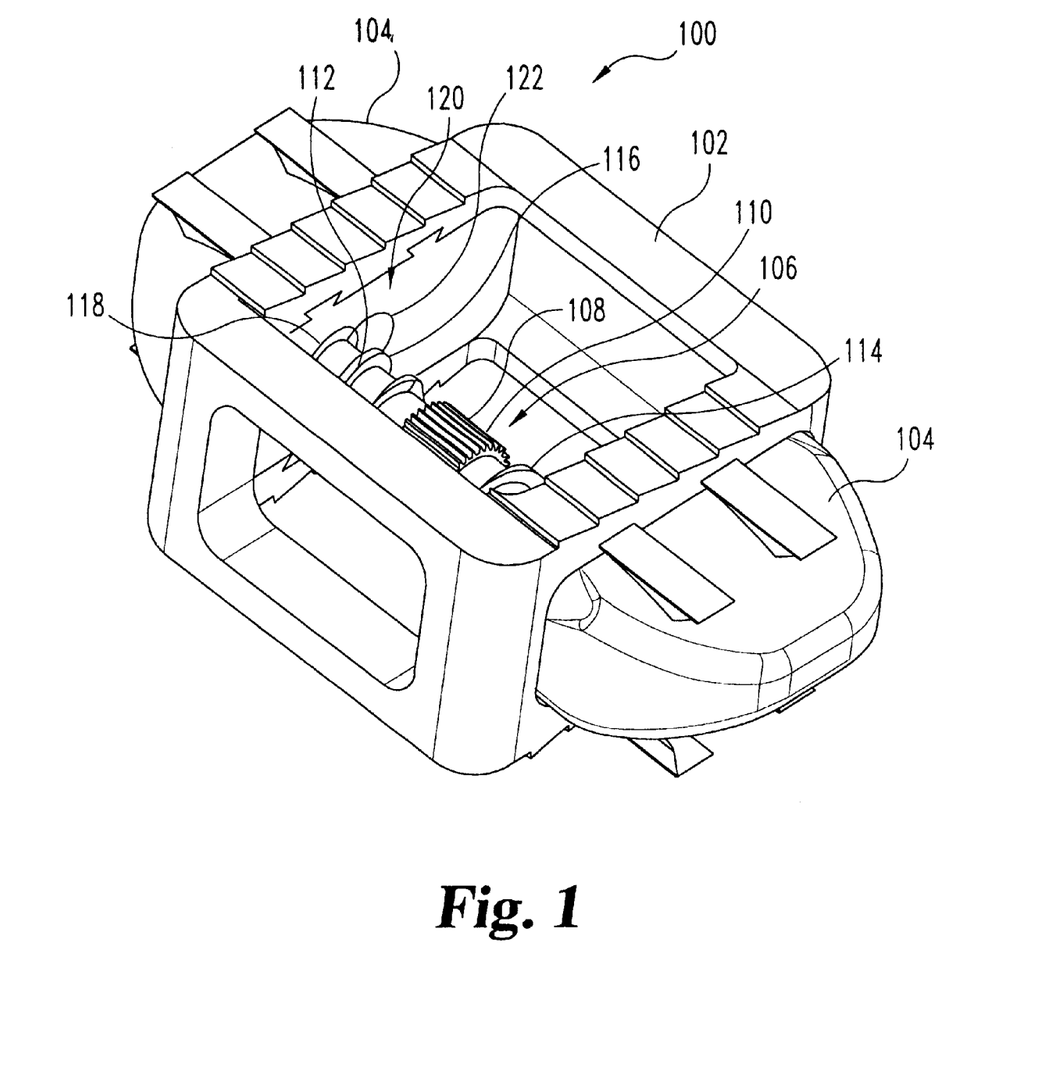
FIG. 1 is a top perspective view of a spinal implant according to one embodiment in an expanded configuration.
Figure 2:
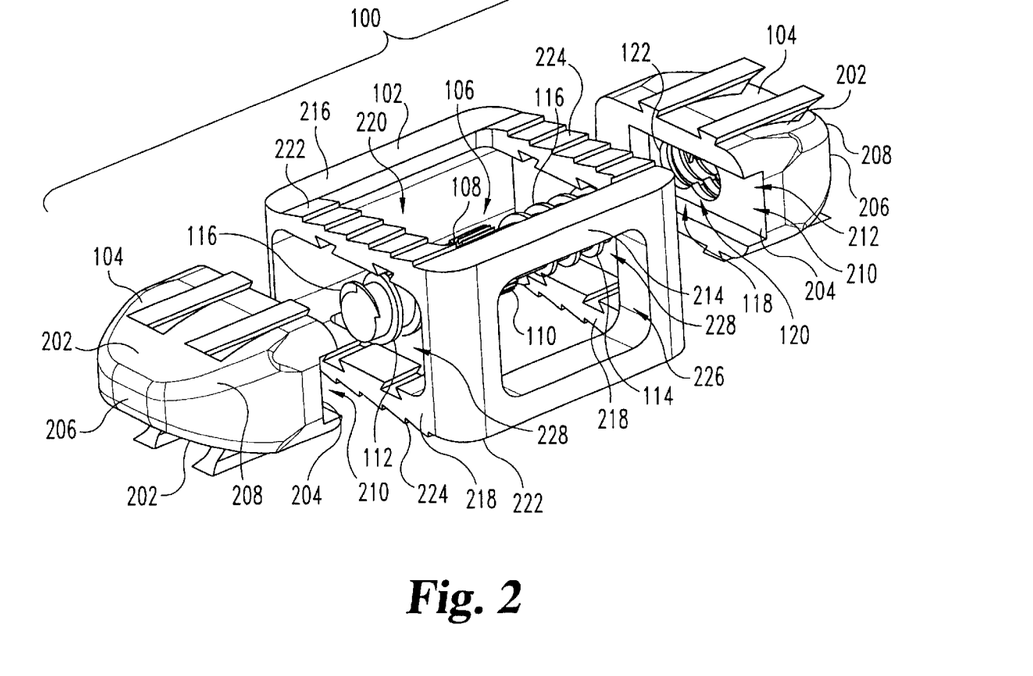
FIG. 2 is an exploded view of the FIG. 1 implant.

A laterally expandable spinal implant 100 according to one embodiment of the present invention will now be described with reference to FIGS. 1–6. As shown in FIGS. 1 and 2, the implant 100 includes a central member or cage 102, a pair of lateral members or wings 104 that are adapted to laterally extend from the cage 102, and an expansion mechanism 106 (or means) that is operable to extend the wings 104. In the illustrated embodiment, the expansion mechanism 106 includes a turnbuckle or threaded shaft 108 that connects the wings 104 together. In other embodiments, the expansion mechanism can include hydraulic pistons, mechanical linkages, and the like. The shaft 108 includes a gear 110 that is centrally located on the shaft 108 between opposing threaded portions 112 and 114. In one embodiment, threads 116 on the threaded portions 112 and 114 are oppositely threaded (i.e., one is a left handed thread and the other is a right handed thread.) In one form of the present invention, the threads 116 of the threaded portions 112 and 114 have an equal pitch such that the wings 104 are able to extend from the central member 102 at the same rate. This ensures that the implant 100 has a symmetrical configuration, which in turn aids in centering the implant 100 over the vertebrae. The threaded portions 112 and 114 threadedly engage threaded openings 118 that are defined in each of the wings 104. In another embodiment, only one end of the shaft 108 is threaded, while the other end of the shaft i08 is unthreaded. With this embodiment, the wings 104 are still extended by rotating the shaft 108.

Implant 100 further includes a lock mechanism 120 that is used to lock the wings 104 in an expanded configuration in which the wings 104 laterally extend from the cage 102. In the embodiment illustrated in FIG. 1, the lock mechanism 120 includes lock cavities 122 that are defined in each of the wings 104 next to the threaded openings 118. As illustrated in FIG. 2, the lock cavities 122 open into the threaded opening 118 in the wings 104. In one embodiment, each lock cavity 122 is only partially threaded such that once the wings 104 are in the expanded configuration, the shaft 108 can be slid from the threaded opening 118 into the lock cavity 122. By being only partially threaded near the entrance of the cavity 122, the shaft 108 is unable to rotate such that the wings 104 are unable to be retracted. In another embodiment, the lock cavity 122 is unthreaded, but has a depth shallower than the threaded openings 118 so as to keep the wings 104 in the expanded configuration, when the shaft is moved into the lock cavities 122.

Referring to FIG. 2, each wing 104 includes opposing vertebrae engaging surfaces 202 that are configured to engage opposing vertebrae, as well as medial 204 and lateral 206 side surfaces. As shown, the wings 104, according to the illustrated embodiment, have a generally tapered shape so as to coincide with the vertebral endplate geometry. The vertebrae engaging surfaces 202 generally taper from the medial sides 204 to the lateral sides 206. To further reduce trauma upon insertion of the implant 100, the wings 104 have beveled edges 208 between the vertebrae engaging surfaces 202 and the lateral surfaces 206. In the illustrated embodiment, the medial sides of the wings 104 are generally flat so as to allow the wings 104 to contact one another in a compact state when the wings 104 are retracted within the cage 102. The medial sides 204 of the wings 104 define access channels 210 around the threaded opening 114 and the lock cavity 122. In one form, access channel 210 is sized to receive the gear 110 on the shaft 108. The access channel 210 has an opening 212 that allows the physician to gain access and rotate the gear 110 so as to expand the implant 100. In the illustrated embodiment, the lateral sides 206 have a generally curved shape in order to coincide with the shape of the apophyseal ring of the vertebrae.

With continued reference to FIG. 2, the cage 102 has a proximal or tool engaging end wall portion 214, an opposite distal end wall portion 216, and a pair of opposing lateral wall portions 218 that together define an interior cavity 220. The cage 202 further has a pair of opposing vertebrae engaging surfaces 222 that are configured to engage opposing vertebrae. To coincide with vertebrae geometry, surfaces 222 in the illustrated embodiment are tapered such that surfaces 222 angle towards one another from the proximal end wall portion 214 to the distal end wall portion 216. As shown, the interior cavity 220 extends through both vertebrae engaging surfaces 222. In the illustrated embodiment, the cage 102 has a generally rectangular shape. The vertebrae engaging surfaces 222 can include texturing so as to prevent expulsion of the implant 100 from the vertebrae. For instance, the vertebrae engaging surfaces 222 in the illustrated embodiment have ridges 224 that aid in preventing expulsion of the implant 100. As should be appreciated, in other forms of the present invention, the vertebrae engaging surfaces 222 can include other types of texturing for preventing expulsion of the implant 100. The proximal end wall portion 214 defines a tool opening 226 through which an insertion tool can be inserted into the interior cavity 220, and lateral walls 218 define wing openings 228 through which the wings 104 are slidably received into the interior cavity 220.

Figure 3:
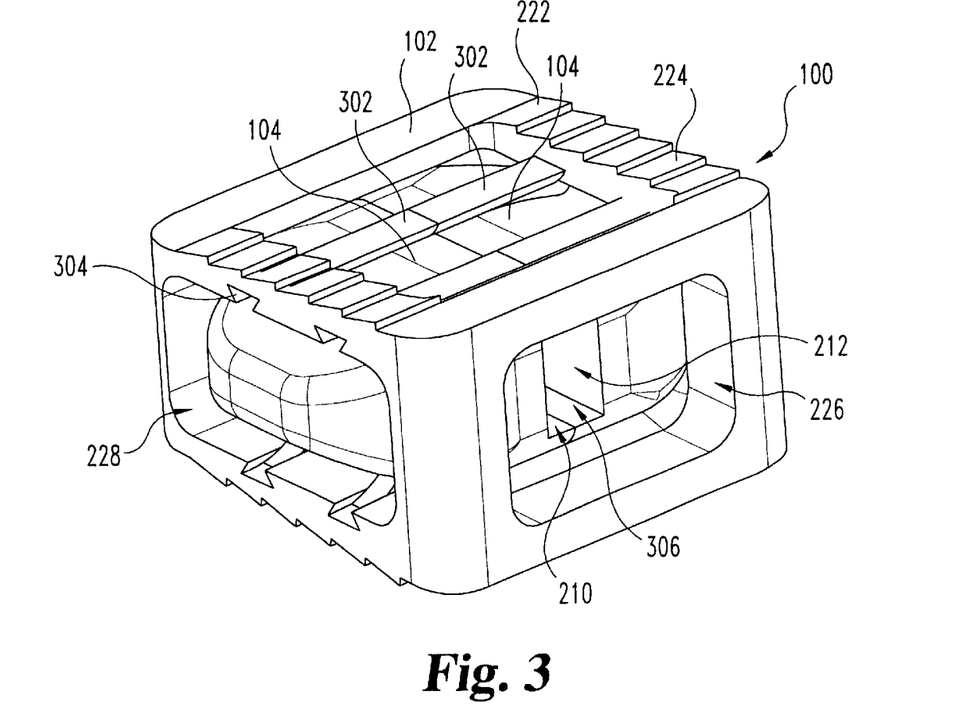
FIG. 3 is a top perspective view of the FIG. 1 implant in a compact configuration.
Figure 4:
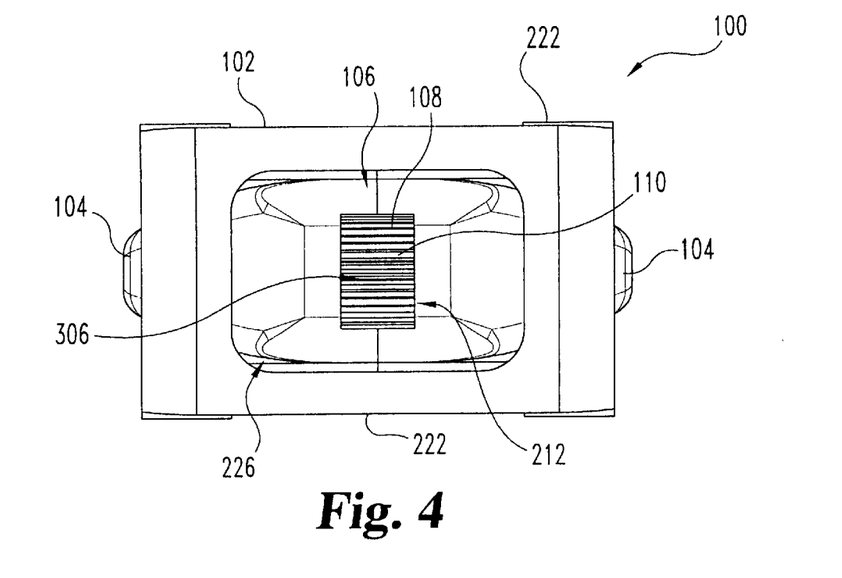
FIG. 4 is an end view of the FIG. 1 implant in a compact configuration.

FIGS. 3 and 4 illustrate the implant 100 when in a compact state in which the wings 104 are retracted inside the interior cavity 220. As shown in FIG. 3, the wings 104 have one or more guide rails 302 that engage corresponding guide channels 304 formed around the wing openings 228. In the illustrated embodiment, each wing 104 has four guide rails, with a pair positioned along each opposing vertebrae engaging surface 202 of the wing 104. In order to provide further stability, the guide rails 302 and the corresponding channels 304 in the illustrated embodiment have a general dovetail shape. Moreover, as discussed in further detail below, the dovetail shape of the guide rails 302 ensure that the wings 104 remain secure in the vertebrae once implanted. When the implant 100 is in a compact state, the majority of the wings 104 are received in the interior cavity 220 of the cage 102. In the compact state, the medial sides 204 contact each other and the entrances 212 of the access channels 210 define an access opening 306 through which an insertion tool can gain access to gear 110 on shaft 108 in order to rotate the shaft 108.

Figure 5:
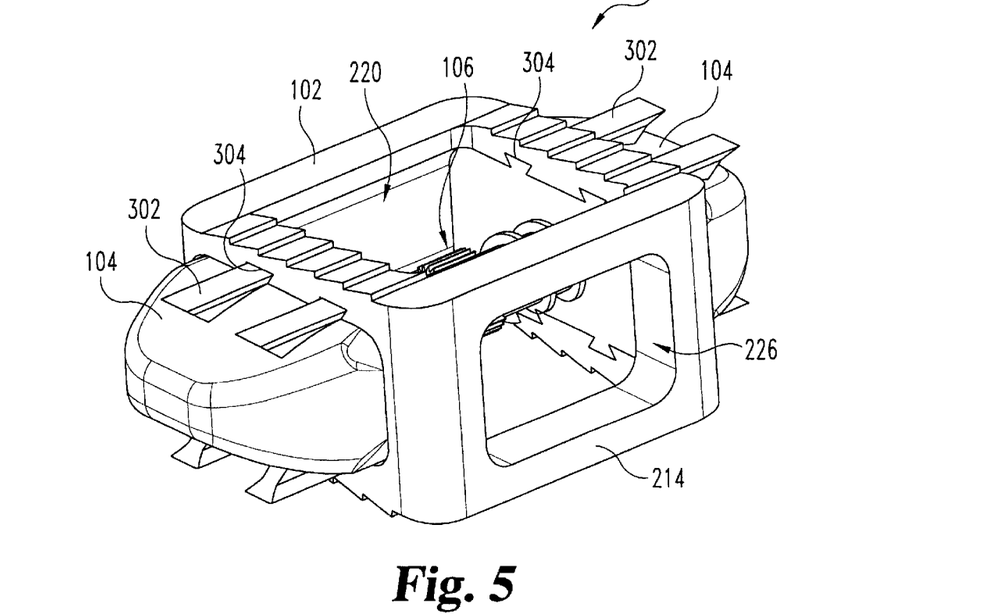
FIG. 5 is a top perspective view of the FIG. 1 implant in an expanded configuration.
Figure 6:
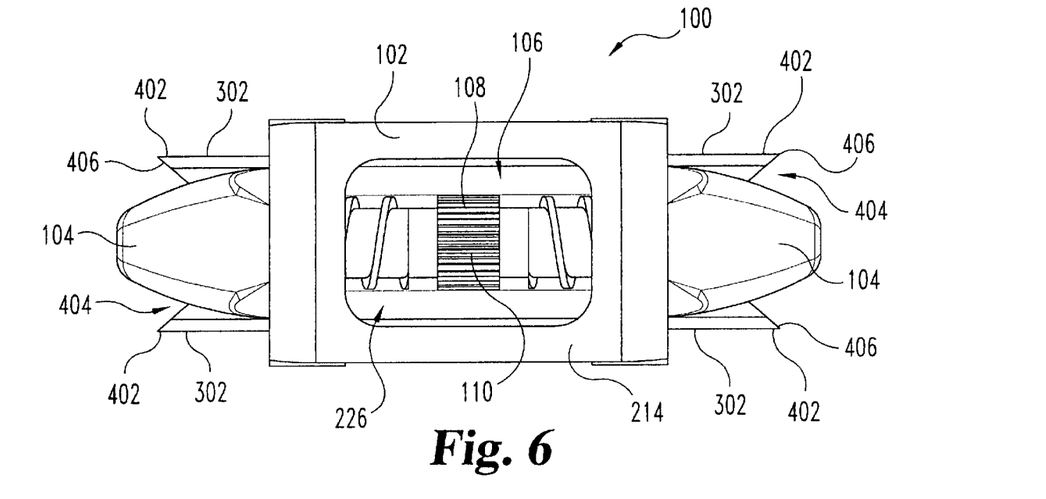
FIG. 6 is an end view of the FIG. 1 implant in an expanded configuration.

As previously mentioned, the gear 110 is used to rotate the shaft 108, thereby causing the wings 104 to extend from the cage 102. FIGS. 5 and 6 show the implant 100 with the wings 104 in a laterally expanded state in which the wings 104 extend from the cage 102. As should be appreciated, the expansion mechanism 106 allows the wings 104 to extend at varying distances from the cage 102 such that the size of the implant 100 can be adjusted to correspond to the size of the selected vertebrae. As shown in FIG. 6, outer lateral ends 402 of the guide rails 302 define an inward notch 404 such that the outer lateral ends 402 form cutting edges 406. As the wings 104 are extended, the cutting edges 406 cut channels into the vertebrae. The cutting edges 406 act like spikes to embed the wings 104 into the vertebral endplates. Once the wings 104 are extended, the dovetail shape of the guide rails 302 help to ensure that the wings 104 are firmly secured to the vertebrae. Once the wings 104 are in the desired extended position, the shaft 108 is then slid into the lock cavity 122 (FIG. 2) in order to lock the wings 104 in the desired extended position. After implantation, bone graft material can be packed into the interior cavity 220 via tool opening 226 to promote fusion of the vertebrae. With the wings 104 slightly extended, bone graft material can even be packed before implantation. Following implantation, the interior cavity 220 provides a large area in which a fusion mass can be formed between the vertebrae.

Figure 7:
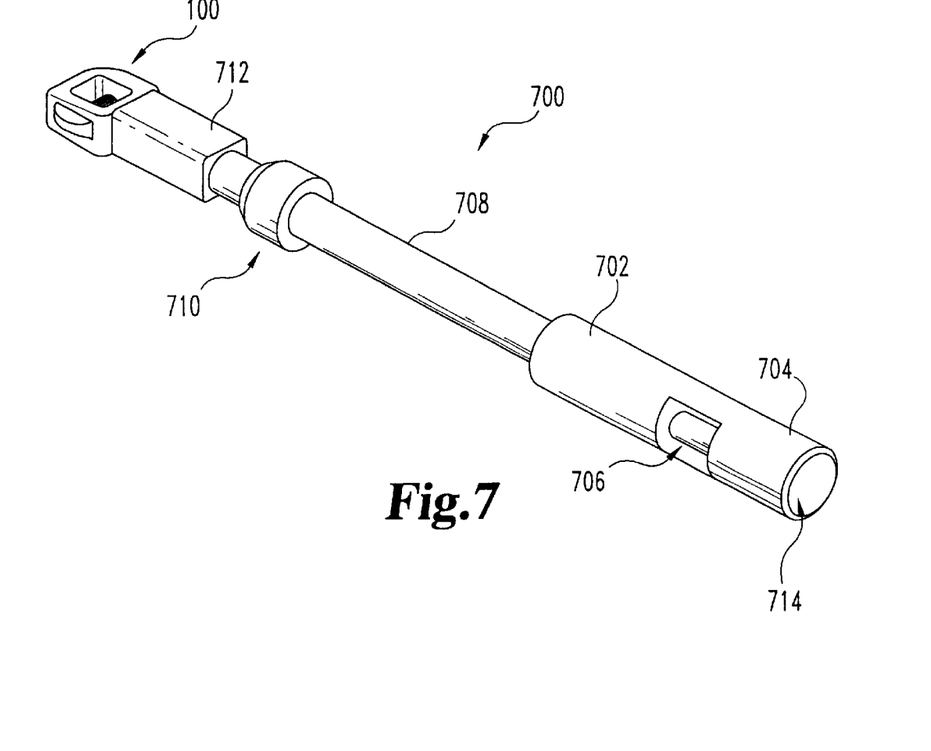
FIG. 7 is a perspective view of the FIG. 1 implant attached to an inserter tool.
Figure 8:
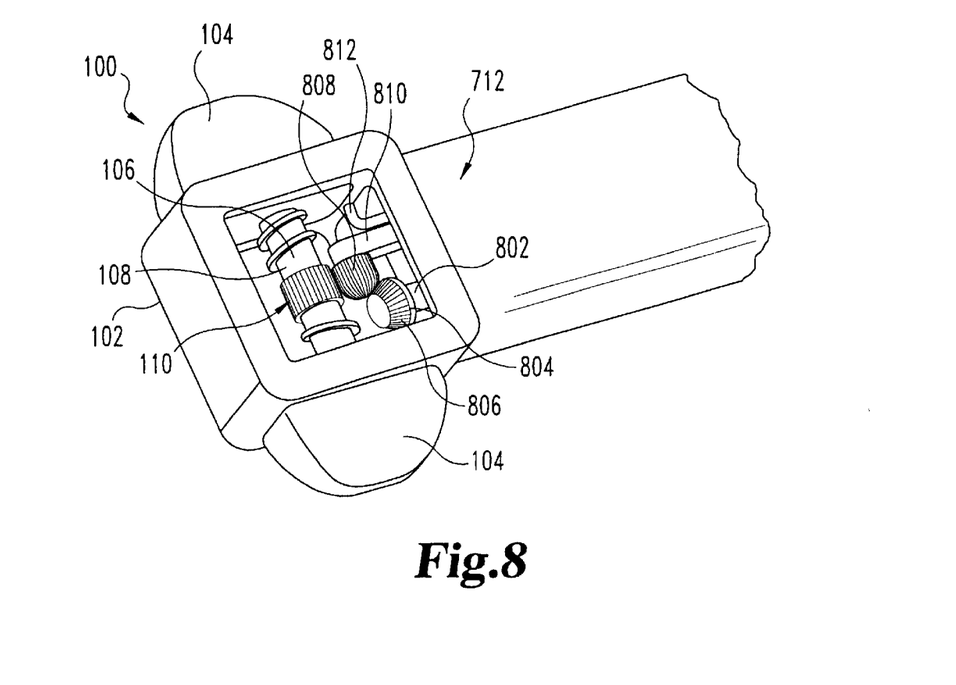
FIG. 8 is an enlarged, perspective view of the FIG. 1 implant coupled to the FIG. 7 tool.

An implant inserter assembly 700 that includes the implant 100 coupled to an inserter 702 according to one embodiment of the present invention is illustrated in FIGS. 7 and 8. The inserter 702 includes a driving handle 704, an actuation knob 706, a shaft portion 708, a gripping knob 710 and a head portion 712. In the illustrated embodiment, the handle portion 704 is solid and includes an impaction surface 714 against which a hammer or the like can strike to drive implant 100 between the vertebrae. The actuation knob 706 is connected to a drive shaft 802, which extends from the actuation knob 706, through the shaft 708, and through the head 712. When the implant 100 engages the inserter 702, the actuation knob 706 is able to extend the wings 104. As shown in FIG. 8, the drive shaft 804 has at one end a drive gear 804 with teeth 806 that engage an intermediate gear 808 that is coupled to the head 712 through a carrier member 810. During implantation, the intermediate gear 808 engages gear 110 on the shaft 108 of the implant 100. As the actuation knob 706 is rotated, the drive shaft 802 rotates drive gear 804. In turn, the drive gear 804 rotates the intermediate gear 808, which then is used to rotate the shaft 108 in order to extend the wings 104. The gripping knob 710 is rotated in order to extend gripping fingers 812 inside the interior cavity 220 such that the inserter 702 engages the tool opening 226 of the implant 100. The gripping knob 710 and the gripping fingers 812 can be optional, such that in one embodiment knob 710 and fingers 812 are not included. To provide a large surface area for impaction, the head 712 has a generally rectangular shape to generally coincide with the shape of the proximal end wall portion 214 of the implant 100.

Figure 9:
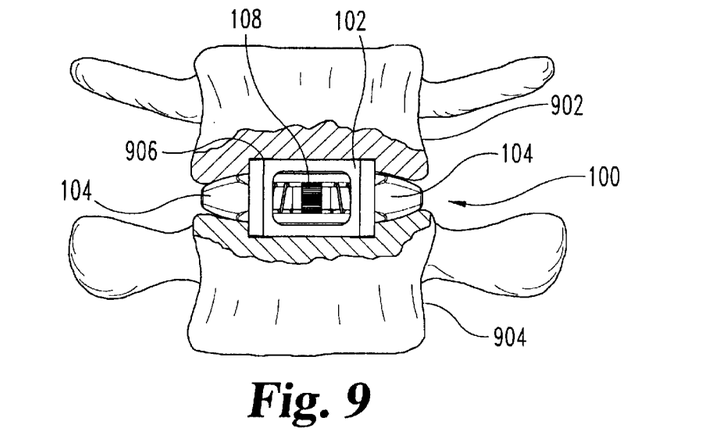
FIG. 9 is a partial cross-sectional view of the FIG. 1 implant positioned in an interdiscal space in an expanded configuration.
Figure 10:
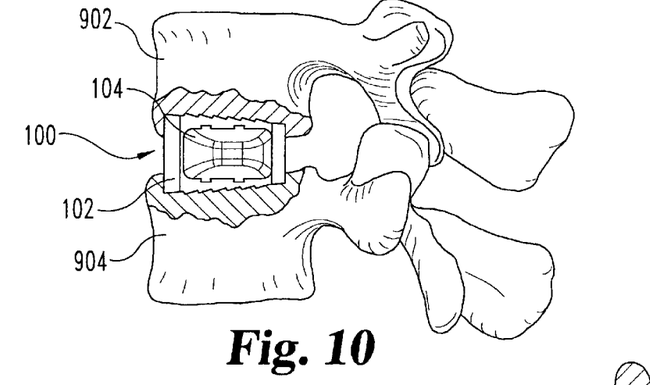
FIG. 10 is a side view of the FIG. 1 implant in the interdiscal space.
Figure 11:
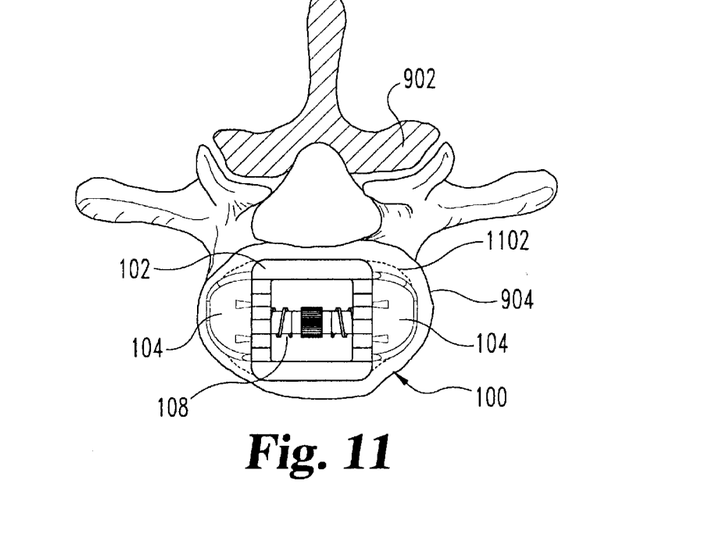
FIG. 11 is a top view of the FIG. 1 implant in the interdiscal space.

FIGS. 9, 10 and 11 show various views of the implant 100 when implanted between adjacent vertebrae 902 and 904. Before implantation, a portion of the annulus is removed to create a larger disc space for the implantation of the implant 100. The vertebral end plates are prepared by removing cartilaginous material connected to them. A window 906, which generally corresponds in shape and size to the cage 102, is formed in both vertebrae 902 and 904. Before implantation, the wings 104 are positioned in their retracted position inside the interior cavity 220 of the implant 100, and the implant 100 is attached to the inserter 702 in the manner as illustrated in FIG. 7. The implant 100 is then impacted into the window 906 formed between vertebrae 902 and 904. Rotation of the actuation knob 706 on the inserter 702 causes the shaft 108 on the implant 100 to rotate, thereby expanding the implant 100. As previously mentioned, this causes the wings 104 to laterally expand from the cage 102 between the vertebrae. In one embodiment, the wings 104 are extended from the cage 102 at the same rate to ensure that the implant 100 remains centered between the vertebrae 902 and 904. As the wings 104 extend, the cutting edges 406 of the guide rails 302 cut into the vertebrae 902 and 904, thereby ensuring that the implant is securely fastened to the vertebrae 902 and 904. The wings 104 are expanded until they are positioned over the apophyseal ring, which contains the harder cortical bone. As shown in FIG. 9, the shape of the wings 104 generally correspond to the geometry of the end plates of vertebrae 902 and 904. Due to the large surface area provided by the implant 100 and by being supported on the harder cortical bone of the apophyseal ring, the risk of subsidence of the implant 100 into the vertebrae 902 and 904 is reduced. Moreover, the construction of implant 100 allows for the implant to have variable dimensions such that the implant 100 can accommodate vertebrae of varying sizes. Once the implant 100 has been expanded to the desired expansion configuration, the turnbuckle 108 can be moved into the block cavity 122 such that the wings 104 are locked into position.

Figure 12:
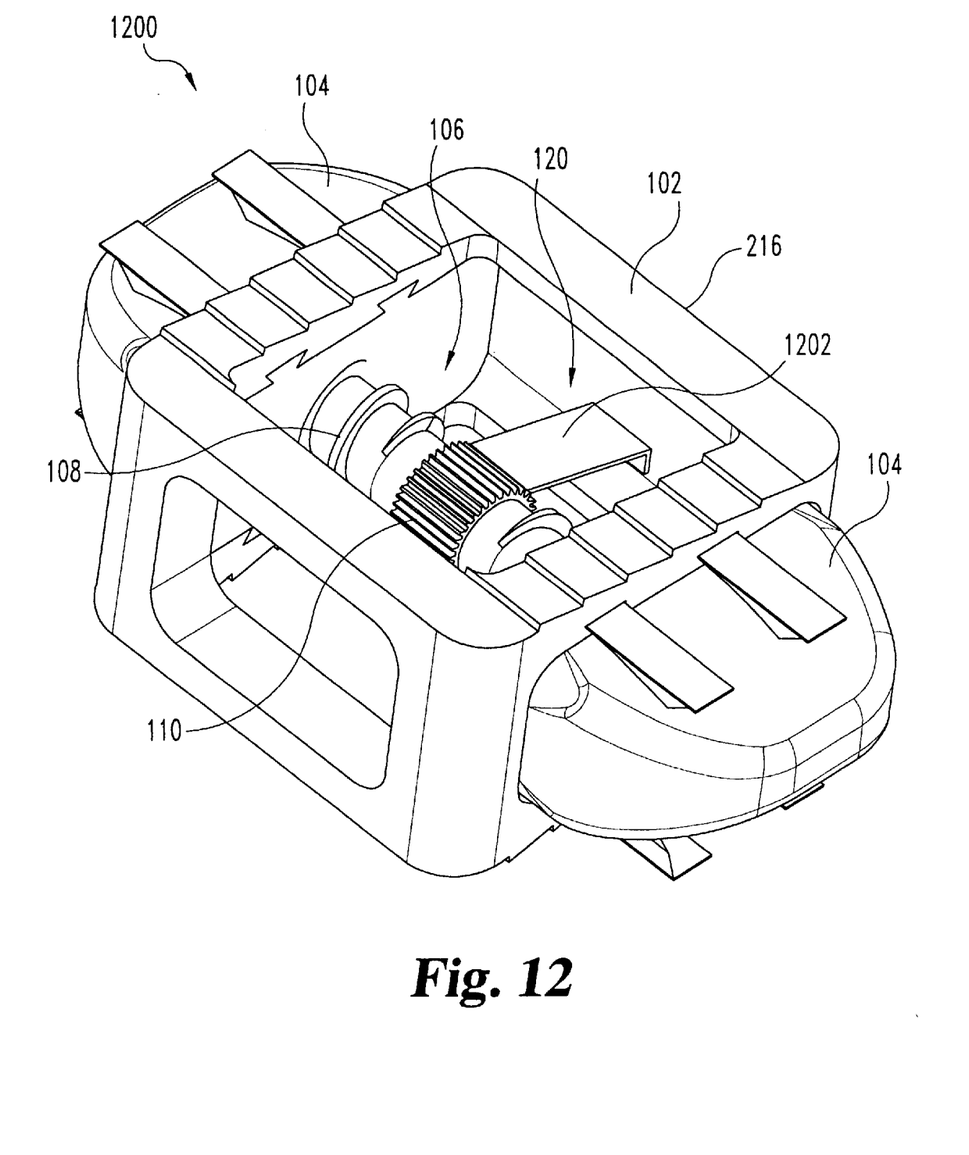
FIG. 12 is a perspective view of a spinal implant according to another embodiment.

Referring to FIG. 12, an implant 1200 according to another embodiment of the present invention incorporates a number of the same features described above, with the exceptions noted below. As should be appreciated, the locking mechanism 120 in this embodiment differs from the one described above. In the embodiment illustrated in FIG. 12, the locking mechanism 120 includes a leaf spring 1202 that is attached to the distal end wall portion 216 of the cage 102. As shown, the leaf spring 1202 engages the gear 110 on the shaft 108. The leaf spring 1202 is positioned such that the shaft 108 can only be rotated in one direction so that the wings 104 can only move in a laterally expanding direction. The spring 1202 resists rotation of the shaft in the opposite direction, so that once the wings 104 are extended to the desired location the spring 1202 locks the wings 104 into position.

While specific embodiments of the invention have been shown and described in detail, the breadth and scope of the present invention should not be limited by the above described exemplary embodiments, but should be defined only in accordance with the following claims and their equivalents. It is understood that only selected embodiments have been shown and described and that all changes and modifications that come within the spirit of the invention are desired to be protected.

What is claimed is:

1. A spinal implant, comprising:
   a cage defining an interior cavity;
   an expansion mechanism received in said cavity of said cage;
   a pair of wings operatively coupled to said expansion mechanism, said wings each having opposing vertebrae engaging surfaces that are configured to engage opposing vertebrae; and
   wherein said expansion mechanism is operable to laterally move said wings between the vertebrae from a compact configuration in which at least a majority of said wings are received in said cavity of said cage to an expanded configuration in which said wings extend from said cage with said vertebrae engaging surfaces on each of said wings engaging the vertebrae.

2. The implant of claim 1, wherein said expansion mechanism includes a shaft having threaded portions on opposite ends that threadedly engage said wings.

3. The implant of claim 2, wherein said shaft includes a gear positioned between said threaded portions for rotating the shaft.

4. The implant of claim 2, wherein said threaded portions are oppositely threaded and have equal thread pitch.

5. The implant of claim 2, further comprising a lock mechanism operable to lock said wings in said expanded configuration.

6. The implant of claim 5, wherein:
said lock mechanism includes lock cavities defined in said wings; and
said lock cavities are configured to prevent rotation of said shaft when said shaft is positioned within said lock cavities.

7. The implant of claim 6, wherein only a portion of each of said lock cavities is threaded.

8. The implant of claim 5, wherein said lock mechanism includes a leaf spring engaged to said cage, said leaf spring being operable to at least prevent rotation of said shaft in one direction.

9. The implant of claim 8, wherein said shaft includes a gear engageable with said leaf spring.

10. The implant of claim 1 further comprising a lock mechanism to lock said wings in an expanded configuration.

11. The implant of claim 10, wherein said lock mechanism included lock cavities constructed and arranged to lock said wings in said expanded configuration.

12. The implant of claim 10, wherein said lock mechanism includes a leaf spring coupled to said cage.

13. The implant of claim 1, wherein said cage has a generally rectangular cross-sectional shape.

14. The implant of claim 1, wherein said cage defines a tool opening for providing access to said cavity.

15. The implant of claim 1, wherein said cage defines wing openings on opposite sides of said cage in which said wings are slidably received.

16. The implants of claim 15, wherein:
at least one of said wing openings defines a guide channel; and
at least one of said wings has a guide member slidably received in said guide channel.

17. The implants of claim 16, wherein said guide member has a dovetail cross-sectional shape.

18. The implant of claim 17, wherein said guide member has a cutting edge operable to cut one of the vertebrae during extension of said wings.

19. The implant of claim 16, wherein said guide member has a cutting edge operable to cut one of the vertebrae during extension of said wings.

20. The implant of claim 1, wherein said cage has opposing surfaces configured to engage the vertebrae.

21. The implant of claim 20, wherein said opposing surfaces are textured surfaces to prevent expulsion of said implant.

22. The implant of claim 21, wherein said textured surfaces include ridges.

23. The implant of claim 1, wherein said vertebrae engaging surfaces of said wings are contoured to correspond in shape to the vertebrae.

24. The implant of claim 1, wherein at least one of said wings has a guide rail received in a guide rail channel defined in said cage.

25. The implant of claim 24, wherein said guide rail has a dovetail cross-sectional shape.

26. The implant of claim 24, wherein said guide rail has an outer cutting edge constructed and arranged to cut the vertebrae during extension of said wings.

27. The implant of claim 1, wherein said cage has oppositely facing vertebrae engagement surfaces and said interior cavity extends between said vertebrae engagement surfaces of said cage.

28. The implant of claim 1, wherein wings define an access opening for allowing access to said expansion mechanism when said wings are in said compact configuration.

29. A spinal implant, comprising:
a cage defining an interior cavity;
an expansion mechanism received in said cavity of said cage;
a pair of wings operatively coupled to said expansion mechanism;
wherein said expansion mechanism is operable to laterally move said wings between the vertebrae from a compact configuration in which at least a majority of said wings are received in said cavity of said cage to an expanded configuration in which said wings extend from said cage to engage the vertebrae;
wherein the vertebrae have apophyseal rings; and
wherein said wings have a generally arcuate shape to coincide with the shape of the apophyseal rings of the vertebrae.

30. The implant of claim 29, wherein said wings each have opposing vertebrae engaging surfaces that are configured to engage opposing vertebrae when in said expanded configuration.

31. A fusion device for implanting between opposing vertebrae that define a disc space, comprising:
a central member;
at least one pair of lateral members slidably coupled to said central member;
means for extending said lateral members from said central member into the disc space between the vertebrae; and
wherein the opposing vertebrae having apophyseal seal rings, said lateral members being shaped to engage the apophyseal seal rings of both opposing vertebrae when extended.

32. The fusion device of claim 31, wherein said means for extending said lateral members includes a shaft with threaded portions coupled to said lateral members.

33. An apparatus, comprising:
a spinal implant including
a central member defining an interior cavity and a pair of openings defined on opposite sides of said central member that open into said interior cavity,
a pair of wings slidably received in said openings in said central member, and
a shaft coupled to said wings, said shaft having at least one threaded portion threadedly engaging at least one of said wings.

34. The apparatus of claim 33, wherein:
said openings have guide channels; and
said wings have guide rails slidably received in said guide channels.

35. The apparatus of claim 33, wherein said at least one threaded portion has a pair of oppositely threaded portions at opposite ends of said shaft.

36. The apparatus of claim 33, further comprising an inserter engaged with said implant to extend said wings.

37. The apparatus of claim 36, wherein said shaft on said spinal implant includes a gear.

38. The apparatus of claim 37, wherein said inserter includes:
an actuation knob;
a drive shaft coupled to said knob;
a drive gear coupled to said drive shaft; and
an intermediate gear engaging said drive gear and said gear on said shaft of said spinal implant.

* * * * *